United States Patent [19]
Gassman

[11] Patent Number: 5,532,925
[45] Date of Patent: Jul. 2, 1996

[54] CURRENT-TO-PRESSURE TRANSDUCER WITH SELECTABLE, ADJUSTABLE INPUT FILTER

[75] Inventor: George W. Gassman, Marshalltown, Iowa

[73] Assignee: Fisher Controls International, Inc., Clayton, Mo.

[21] Appl. No.: 290,015

[22] Filed: Aug. 12, 1994

[51] Int. Cl.$^6$ .................................................. G05B 13/02
[52] U.S. Cl. .................... 364/177; 364/183; 364/558; 364/572
[58] Field of Search .................................. 364/148, 152, 364/176, 177, 509, 510, 558, 572, 183

[56] References Cited

U.S. PATENT DOCUMENTS

| | | | |
|---|---|---|---|
| 3,602,487 | 8/1971 | Johnson | 263/19 A |
| 3,663,833 | 5/1972 | Pao et al. | 364/510 X |
| 3,965,548 | 6/1976 | James, II et al. | 28/1.7 |
| 4,006,346 | 2/1977 | Pemberton | 235/150.1 |
| 4,035,620 | 7/1977 | Hobbs et al. | 364/181 |
| 4,094,959 | 6/1978 | Ball et al. | 364/161 X |
| 4,106,916 | 8/1978 | Tuckett et al. | 55/21 |
| 4,119,837 | 10/1978 | Sheldon et al. | 235/92 MP |
| 4,246,070 | 1/1981 | Hofferber | 196/132 |
| 4,249,908 | 2/1981 | Funk | 23/230 A |
| 4,257,105 | 3/1981 | Stewart et al. | 364/501 |
| 4,369,026 | 1/1983 | Morgan et al. | 431/12 |
| 4,509,000 | 4/1985 | Ferguson | 364/181 X |
| 4,562,528 | 12/1985 | Baba | 364/133 |
| 4,836,011 | 6/1989 | Dombrowski et al. | 73/4 R |
| 4,866,441 | 9/1989 | Conway et al. | 364/178 X |
| 4,901,756 | 2/1990 | Rovner | 137/487.5 |
| 4,976,144 | 12/1990 | Fitzgerald | 73/168 |
| 5,182,704 | 1/1993 | Bengtsson | 364/148 |
| 5,197,328 | 3/1993 | Fitzgerald | 73/168 |
| 5,249,138 | 9/1993 | Piety, Jr. et al. | 364/132 X |

OTHER PUBLICATIONS

Fisher Controls Company, "Industrial Process Control," First Edition, 1971, Sheldon G. Lloyd and Gerald D. Anderson, pp. 61–62.

*Primary Examiner*—Joseph Ruggiero
*Attorney, Agent, or Firm*—Marshall, O'Toole, Gerstein, Murray & Borun

[57] ABSTRACT

Apparatus responsive to a control signal for developing a pressure includes a current-to-pressure transducer including a transducer responsive to the control signal for developing the pressure and a filter disposed intermediate the control signal and the current-to-pressure transducer. The filter has a dynamic input-to-output characteristic with an adjustable time constant so that the dynamic input-to-output characteristic can be varied. The apparatus also includes a signal selector for selectively activating and deactivating the filter.

18 Claims, 2 Drawing Sheets

5,532,925

CURRENT-TO-PRESSURE TRANSDUCER WITH SELECTABLE, ADJUSTABLE INPUT FILTER

TECHNICAL FIELD

The present invention relates generally to current-to-pressure transducers and, more particularly, to a current-to-pressure transducer having a selectable, adjustable input filter.

BACKGROUND ART

Control systems, such as for controlling liquid or gas flow processes, typically include a current-to-pressure transducer coupled to an actuator which, in turn, is coupled to a valve which controls a process. An output signal from a process controller is coupled to the current-to-pressure transducer for controlling the process.

In an open-loop process control system, the process controller supplies a 4–20 mA control signal to the current-to-pressure transducer which converts the control signal into an output pressure causing the actuator to operate the valve to control the process in a predetermined manner. In contrast, in a closed-loop process control system, a sensor detects the value of a parameter of the process being controlled so that the value of the parameter can be fed back to the process controller. The process controller then regulates its output signal continuously to maintain a minimal difference between the value of the sensed process parameter and an input command, called a setpoint or desired value for the sensed process parameter.

In applications where the process to be controlled has a small time constant, it is desirable to employ a current-to-pressure transducer having a slow first-order response in conjunction with a spring-and-diaphragm actuator. One such transducer is the Type 546 current-to-pressure transducer, manufactured by Fisher Controls International, Inc. This transducer is functionally similar in its response characteristic to a single-pole, low-pass filter with a large time constant.

Other developments in transducer technology have given rise to transducers having faster, second-order low-pass filter characteristics when connected to an actuator such as a spring-and-diaphragm actuator. While these transducers can be employed to operate actuators in the closed-loop control of fast processes, the proportional gain of the process controller must be reduced by re-tuning the process controller in order for these transducers to achieve the same degree of process loop damping as transducers having relatively slower, first-order lag characteristics. In some instances, even after the controller is re-tuned in an effort to achieve system stability, the controlled process variable or parameter still exhibits overshoot, or limit cycles (i.e., small amplitude oscillations), or does not conform as closely as desired to the command input signal or setpoint and responds more slowly than is desired to a change in the setpoint.

The foregoing problems arise, for example, when the current-to-pressure transducer must be replaced due to aging or wear caused by constant exposure to vibration, adverse thermal conditions, or ordinary wear, or simply when a technological upgrade of the transducer or other system components is desired. In such cases, changes in the response characteristic of the transducer and actuator from a first-order to a second-order lag characteristic can adversely affect process loop tuning and control.

SUMMARY OF THE INVENTION

The present invention provides a current-to-pressure transducer having a selectable, adjustable input filter which overcomes the problems described above.

In accordance with one aspect of the present invention, an apparatus responsive to a control signal for developing a pressure includes a current-to-pressure transducer including means responsive to the control signal for developing the pressure and a filter disposed intermediate the control signal and the current-to-pressure transducer. The filter has a dynamic input-to-output characteristic with an adjustable time constant so that the dynamic input-to-output characteristic may be varied. The apparatus also includes means for selectively activating and deactivating the filter. Preferably, the filter comprises an integral part of the current-to-pressure transducer.

In one embodiment, the filter is a dominant, first-order lag filter and, preferably, is a low-pass filter. The filter may include an operational amplifier and may further include a resistor-capacitor network coupled to the operational amplifier. Alternatively, the filter may be a digital filter and may include calculating means for performing digital calculations to derive the dynamic input-to-output characteristic. Preferably, the calculating means in the latter embodiment includes a microprocessor.

In a system for controlling a process having a process parameter, wherein the system includes detecting means for detecting the process parameter, a controller having means for receiving an input signal derived from the detected process parameter and means for deriving a controller output signal which depends on the input signal, a current-to-pressure transducer responsive to the controller output signal for developing a pressure, a valve actuator responsive to the pressure developed by the transducer, and a valve responsive to the valve actuator for controlling the process, the present invention provides an improvement comprising a filter disposed intermediate the control signal and the current-to-pressure transducer, the filter having a dynamic input-to-output characteristic which substantially ensures that the gain of the system is small enough to substantially maintain the stability of the system and large enough to enable the process parameter to be adjusted to substantially compensate for load variations in the process. The dynamic input-to-output characteristic of the filter has a user-adjustable time constant so that the dynamic input-to-output characteristic may be varied. Further, means are provided for selectively activating and deactivating the filter.

BRIEF DESCRIPTION OF THE DRAWINGS

The features of this invention which are believed to be novel are set forth with particularity in the appended claims. The invention may be best understood by reference to the following description taken in conjunction with the accompanying drawings, in which like reference numerals identify like elements in the several figures and in which:

DESCRIPTION OF THE PREFERRED EMBODIMENTS

Figure 1:
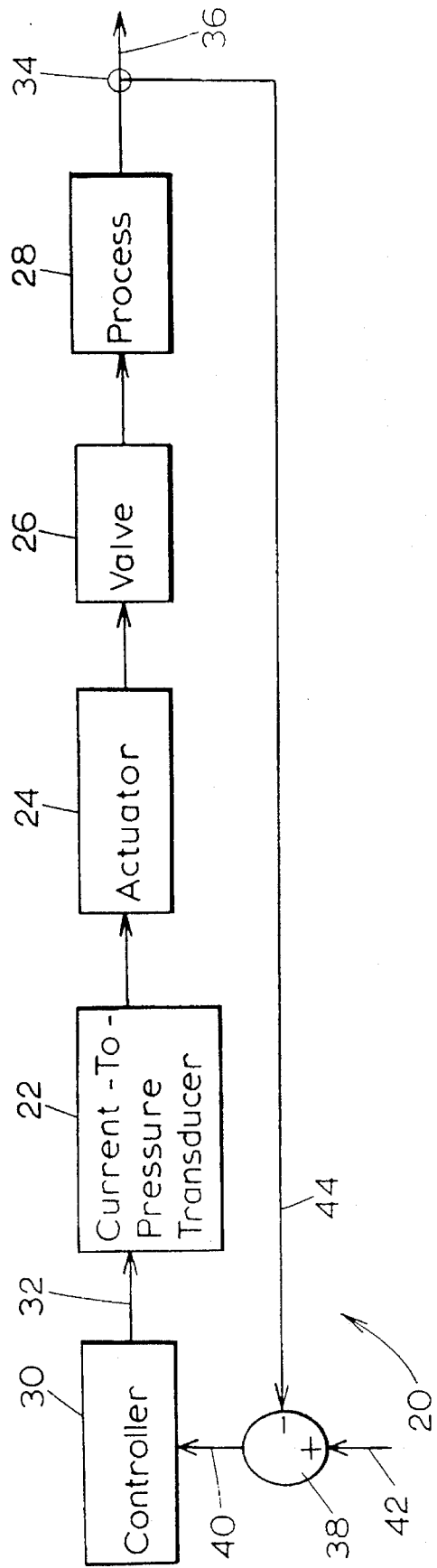
FIG. 1 is a block diagram illustrating a process control loop in which the transducer of the present invention is use.

Referring initially to FIG. 1, a process control system 20 includes a current-to-pressure transducer 22 coupled to a valve actuator 24 which, in turn, is coupled to a valve 26 which controls a process 28. The process 28 may be a flow process, a liquid pressure process, or a small-volume gas pressure process, or any other desired process. A process controller 30 supplies a 4–20 mA control signal 32 to the current-to-pressure transducer 22 to control the process 28.

The process control system 20 may be an open-loop or a closed-loop system. In a closed-loop system (shown in FIG. 1), a sensor 34 operates to detect the value of a process parameter 36, such as a flow rate or pressure, a temperature, a liquid level, a specific gravity, or any other desired parameter. The detected value of the parameter 36 is coupled to an inverting input of a summer 38 which computes a difference 40 between an input command signal or setpoint 42 and a signal 44 representing the value of the parameter 36 as detected by the sensor 34. In an open-loop process control system 20 (not shown), the sensor 34 and the summer 38 are omitted., and the input command signal or setpoint 42 is coupled directly to the process controller 30 to control the process 28 in a predetermined manner (i.e., wherein the controller input is not responsive to the value of the detected process parameter 36).

Figure 2:
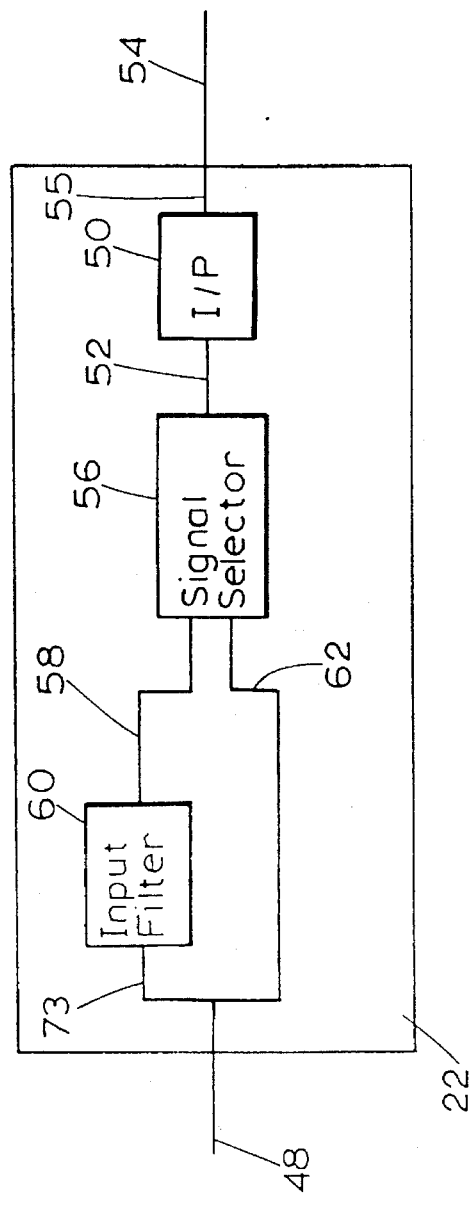
FIG. 2 is a block diagram illustrating a current-to-pressure transducer having a selectable, adjustable input filter in accordance with the present invention.

Referring now to FIG. 2, the current-to-pressure transducer 22 has an input 48 (which typically is either a 4–20 mA current signal or a 1–5 V voltage signal and which, in either case, is proportional to the 4–20 mA control signal 32) and a pressure output 54. The current-to-pressure transducer 22 also includes a transducer 50 having an input 52. The pressure output 54 of the current-to-pressure transducer 22 is coupled directly to an output 55 of the transducer 50.

The input 52 of the transducer 50 is coupled to a signal selector 56 which is operable to select either of two input signals to be coupled to the input 52 of the transducer 50. More particularly, the signal selector 56 operates to select either a filtered signal 58, which is filtered by an input filter 60, or an unfiltered signal 62, which is simply the input 48 to the current-to-pressure transducer 22. In other words, the signal selector 56 is operable to select or de-select the filtering function of the filter 60 so that the current-to-pressure transducer 22 can be operated with or without the selectable, adjustable input filter 60.

Referring now to FIGS. 1 and 2, in installations where the dynamics of the process 28 are dominant in the control system 20, the signal selector 56 is operated to de-select the input filter 60 (i.e., to couple the unfiltered signal 62 to the input 52 of the transducer 50) inasmuch as the dominant, first-order filter is not required in such installations. In other installations, where the dynamics of the process 28 are not dominant, the signal selector 56 is operated to select the input filter 60 (i.e. to couple the filtered signal 58 to the input 52 of the transducer 50) so that the filter 60 may be adjusted to achieve stability of the process control system 20.

Figure 3:
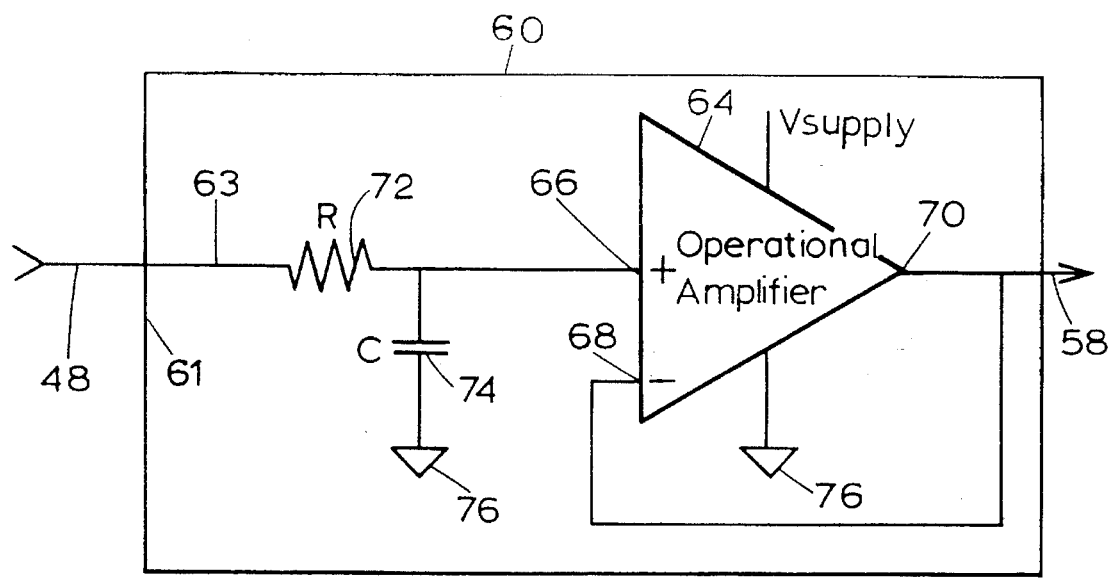
FIG. 3 is a schematic diagram illustrating an analog embodiment of the input filter of FIG. 2.

Referring now to FIG. 3, the input filter 60 is now described in more detail. Initially, it should be noted that while the filter 60 is described below in connection with an analog circuit, it will be readily apparent to those skilled in the art that the filtering function may also be achieved by digital means such as a microprocessor suitably programmed to calculate the same input-to-output characteristic as would be generated by the equivalent analog filter 60 shown in FIG. 3.

As shown in FIG. 3, the input filter 60 includes an operational amplifier 64 having a positive input terminal 66, a negative input terminal 68, and an output terminal 70 at which the operational amplifier 64 produces an output signal. The output signal is fed back from the output terminal 70 to the negative input terminal 68. A resistor 72 is coupled between the input 48 and the positive input terminal 66 of the operational amplifier 64. In addition, a capacitor 74 is coupled between the positive input terminal 66 of the operational amplifier 64 and a ground terminal 76.

The resistance and capacitance values of the resistor 72 and the capacitor 74, respectively, may be chosen to obtain a time constant for the input filter 60 having whatever value is needed for the process control system 20 to be stable. Of course, the value of the time constant will depend on the characteristics of all of the dominant lags present in the process control system 20 as will be evident to those of ordinary skill in the art.

In addition, as an alternative to the use of the above-described signal selector 56 as a means for selecting and deselecting the filter 60, the filter 60 can be effectively deselected by choosing resistance and capacitance values for the resistor 72 and the capacitor 74, respectively, so that the time constant for the filter 60 is very small or zero. In other words, the resistance of the resistor 72 should be small or nearly zero and, in any event, much less than the input impedance of the operational amplifier 64 selected for the application. The capacitor should be of a high-quality, low-leakage type (e.g., fabricated of tantalum or ceramic materials) and should not be sufficiently large to load the input 48 during transients.

In an analog embodiment, the resistance and capacitance values may be selected simply by coupling resistive and capacitive elements having the desired values into the filter 60. Alternatively, in a digital embodiment, a user-defined parameter may be set to a value corresponding to the desired time constant for the filter 60 simply by suitably programing the digital filter (i.e. in either software or firmware programing, as desired). In addition, in the digital embodiment, another user-defined parameter may be used to select and de-select the filter 60, thereby providing, in the digital embodiment, the same functionality as is provided by the signal selector 56 in the above-described analog embodiment of the filter 60.

Of course, it will be readily apparent to those skilled in the art that the filter function of the filter 60 may be provided by any other analog or digital, electrical or mechanical means instead of the op-amp/RC circuit described above and shown in FIG. 3. In any case, what is important is that the filter 60 have a dynamic input-to-output characteristic which substantially ensures that the gain of the process control system 20 (FIG. 1) is small enough to substantially maintain the stability of the system 20 and large enough to enable the process parameter 36 (FIG. 1) to be adjusted to substantially compensate for load variations in the process 28 (FIG. 1). Further, regardless of the type of filter 60 used in the transducer 22, the dynamic input-to-output characteristic of the filter 60 should have a time constant which is adjustable to enable variation of the dynamic input-to-output characteristic as described above. Thus, when a current-to-pressure transducer 22 is installed in a process control system 20, the gain of the input filter 60 is increased to adjust the input-to-output characteristic of the filter 60 while maintaining the stability of the process control system 20.

Figure 4:
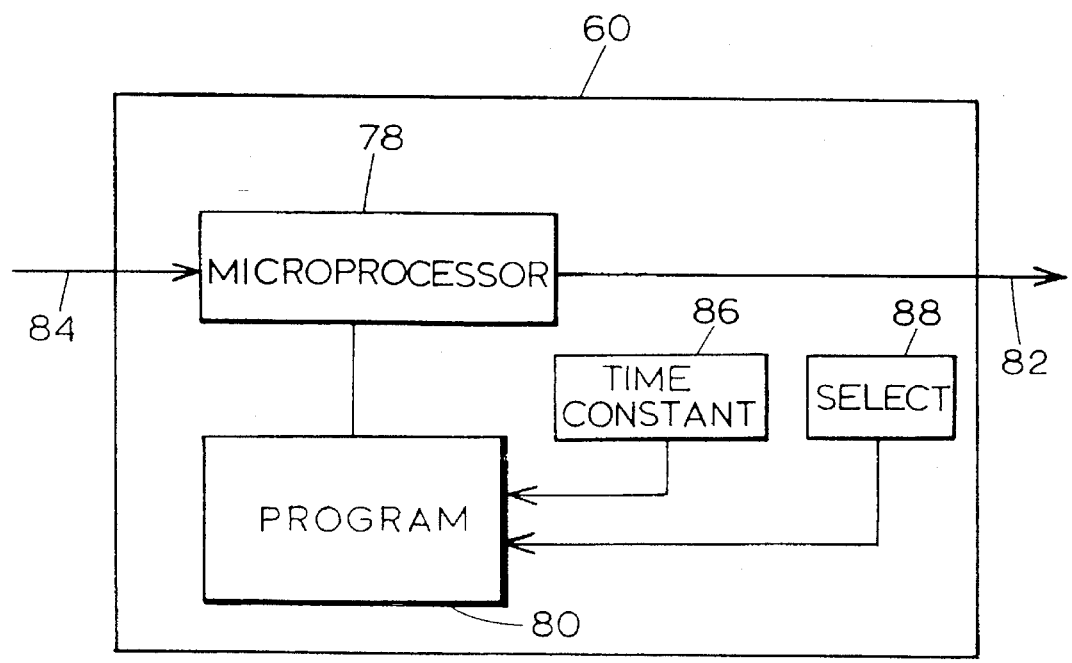
FIG. 4 is a schematic block diagram illustrating a digital embodiment of the input filter of FIG. 2.

Referring now to FIG. 4, the digital embodiment of the filter 60 includes a microprocessor 78 and calculating means such as a program 80 adapted to be executed by the microprocessor 78 to implement the dynamic input-to-output characteristic of the filter 60 by deriving an output bit stream 82 (which may be either parallel or serial) from an input bit stream 84 (which also may be either parallel or serial). To those of ordinary skill in the art, it is a straightforward matter to develop the program 80 to perform the calculations required to implement the digital embodiment of the filter 60. The digital filter 60 also includes a user-defined parameter 86 for choosing a time constant for the filter 60 and a user-defined parameter 88 for selecting and deselecting the filter 60. As an optional additional feature of the digital embodiment, the program 80 may employ a default setting for the time constant when the user-defined parameter 86 is set to zero and the user-defined parameter 88 is set to select the filter 60.

Referring again to FIG. 2, the current-to-pressure transducer 22 may optionally be equipped with a filter 60 which cannot be de-selected, such as by the signal selector 56 described above, for use in those installations in which the filter 60 is always necessary (e.g., installations in which the dynamics of the process 28 will never be dominant in the process control system 20).

A transducer 22 having a selectable, adjustable input filter 60 in accordance with the present invention facilitates relatively quicker response of the process parameter 36 to changes in the setpoint 42 than could be achieved by process control systems 20 employing prior-art, non-filtering current-to-pressure transducers.

The foregoing description is for the purpose of teaching those skilled in the art the best mode of carrying out the invention and is to be construed as illustrative only. Numerous modifications and alternative embodiments of the invention will be apparent to those skilled in the art in view of this description. The details of the disclosed structure may be varied substantially without departing from the spirit of the invention, and the exclusive use of all modifications within the scope of the appended claims is reserved.

What is claimed is:

1. Process control system apparatus responsive to a control signal for developing a pressure, the apparatus comprising:

a current-to-pressure transducer including means responsive to an input signal for developing the pressure;

control signal receiving means for receiving a control signal;

a filter integral with the process control system apparatus and electrically coupled intermediate the control signal receiving means and the current-to-pressure transducer, wherein the filter has a dynamic input-to-output characteristic with a time constant which is adjustable to enable variation of the dynamic input-to-output characteristic; and means for selectively activating the filter so that the filter filters the control signal to develop the input signal to the current-to-pressure transducer and deactivating the filter so that the filter does not filter the control signal to develop the input signal.

2. The apparatus of claim 1, wherein the filter is a dominant, first-order lag filter.

3. The apparatus of claim 1, wherein the filter is a low pass filter.

4. The apparatus of claim 1, wherein the filter includes an operational amplifier.

5. The apparatus of claim 4, wherein the filter further includes a resistor-capacitor network coupled to the operational amplifier.

6. The apparatus of claim 1, wherein the filter is a digital filter.

7. The apparatus of claim 6, wherein the filter includes calculating means for performing digital calculations to derive the dynamic input-to-output characteristic.

8. The apparatus of claim 7, wherein the calculating means includes a microprocessor.

9. In a process control system for controlling a process having a process parameter, wherein the system includes detecting means for detecting the process parameter, a process controller having receiving means for receiving an input signal derived from the detected process parameter and deriving means for deriving a controller output signal which depends on the input signal, a current-to-pressure transducer responsive to the controller output signal for developing a pressure, a valve actuator responsive to the pressure developed by the transducer, and a valve responsive to the valve actuator for controlling the process, the improvement comprising:

a selectively activatable and deactivatable filter integral with and electrically coupled to the current-to-pressure transducer for receiving the control signal and passing a filtered signal to the current-to-pressure transducer when the filter is selectively activated and passing an unfiltered signal to the current-to-pressure transducer when the filter is selectively deactivated;

the filter having a dynamic input-to-output characteristic which substantially ensures that the gain of the system is small enough to substantially maintain the stability of the system and large enough to enable the process parameter to be adjusted to substantially compensate for load variations in the process; and selecting means for selectively activating the filter where the dynamics of the process are not dominant in the process control system so that the filter is required and is adjustable to achieve stability of the process control system and deactivating the filter where the dynamics of the process are dominant in the process control system and the filter is not required to achieve stability of the process control system;

wherein the dynamic input-to-output characteristic of the filter has a time constant which is adjustable to enable variation of the dynamic input-to-output characteristic.

10. The system of claim 9, wherein the filter is a dominant, first-order lag filter.

11. The system of claim 9, wherein the filter is a low-pass filter.

12. The system of claim 9, wherein the filter includes an operational amplifier.

13. The system of claim 12, wherein the filter further includes a resistor-capacitor network coupled to the operational amplifier.

14. The system of claim 9, wherein the filter is a digital filter.

15. The system of claim 14, wherein the filter includes calculating means for performing digital calculations to derive the dynamic input-to-output characteristic.

16. The system of claim 15, wherein the calculating means includes a microprocessor.

17. The system of claim 9, wherein the selecting means comprises means for activating the filter for controlling a process that lacks a dominant first-order lag characteristic and for deactivating the filter for controlling a process that has a dominant first-order lag characteristic.

18. Process control system apparatus responsive to a control signal for developing a pressure, comprising:

a current-to-pressure transducer having a low-pass filter integral therewith;

the current-to-pressure transducer further including pressure-developing means responsive to the control signal for developing the pressure;

the filter disposed intermediate the control signal and the pressure-developing means and having a dynamic input-to-output characteristic with a time constant which is adjustable to enable variation of the dynamic input-to-output characteristic; and means for selectively activating and deactivating the low-pass filter to achieve stability of the process control system, including means for activating the filter for controlling a process that lacks a dominant first-order lag characteristic and for deactivating the filter for controlling a process that has a dominant first-order lag characteristic;

wherein the low-pass filter is a dominant, first-order lag filter and is an integral part of the current-to-pressure transducer; and wherein the low-pass filter is selected from the group consisting of an analog filter including an operational amplifier and a digital filter including calculating means for performing digital calculations to derive the dynamic input-to-output characteristic.

* * * * *